United States Patent [19]

Czech

[11] Patent Number: 4,900,818
[45] Date of Patent: Feb. 13, 1990

[54] LARGE SCALE SYNTHESIS OF TWELVE MEMBER DIAZAMONOCYCLIC COMPOUNDS

[75] Inventor: Bronislaw P. Czech, Peekskill, N.Y.

[73] Assignee: Technicon Instruments Corporation, Tarrytown, N.Y.

[21] Appl. No.: 319,792

[22] Filed: Mar. 6, 1989

Related U.S. Application Data

[63] Continuation-in-part of Ser. No. 132,741, Dec. 14, 1987, abandoned.

[51] Int. Cl.$^4$ .......................................... C07D 273/08
[52] U.S. Cl. ..................................... 540/454; 540/460; 540/469; 558/81
[58] Field of Search .................. 540/454, 460, 469; 558/81

[56] References Cited

U.S. PATENT DOCUMENTS 4,845,212 7/1989 Czech .................................. 540/469

Primary Examiner—Robert T. Bond
Attorney, Agent, or Firm—Jeffrey M. Greenman

[57] ABSTRACT

A process is disclosed for synthesizing large quantities of a compound of formula I

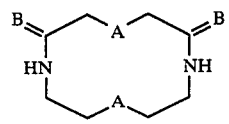

wherein a solution of a compound of formula II

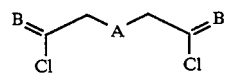

is mixed with a solution of a compound of formula III

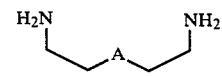

under suitable process conditions, and wherein A, same or different, is N—R, O, S, CRR' or P(O)R, and R and R' are hydrogen, alkyl, alkylidene, aryl, tosyl, allyl or benzyl, and B is O.

Compounds of formula I may be reduced to form an azacorand of formula IV

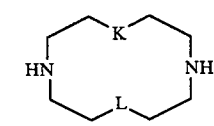

wherein K and L, same or different, are N—R, O, S, CRR', or P(O)R, and R and R' are hydrogen, alkyl, alkylidene, aryl, tosyl, allyl or benzyl.

Also disclosed in a compound of formula IV synthesized in accordance with the above procedure wherein K and L are not both O or S.

13 Claims, No Drawings

LARGE SCALE SYNTHESIS OF TWELVE MEMBER DIAZAMONOCYCLIC COMPOUNDS

This application is a Continuation-In-Part of Application Ser. No. 07/132,141 filed Dec. 14, 1987 now abandoned.

BACKGROUND OF THE INVENTION

The present invention relates to large scale synthesis of twelve member diazamonocyclic compounds and to certain novel and useful compounds prepared thereby.

Lehn, U.S. Pat. Nos. 3,888,877 ('877) and 4,156,683 ('683), describe synthesis of certain macrocyclic compounds and complexes thereof. Both patents issued from continuations-in-part of U.S. application Ser. No. 43,979, filed June 5, 1970, now abandoned. Example 44 (at column 41 of '877 and column 42 of '683) describes preparation of 5,9-dioxo-1,7-dioxa-4,10-diazacyclododecane (4) by reacting 1,5-diamino-3-oxapentane (3) with diglycolic acid dichloride (2) at specified concentrations and reaction conditions. The product 5,9-dioxo-1,7-dioxa-4,10-diazacyclododecane (4) is reduced to form 1,7-dioxa-4,10-diazacyclododecane (1).

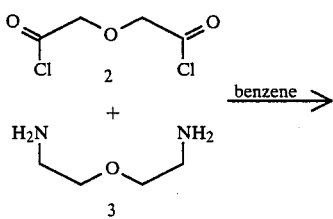

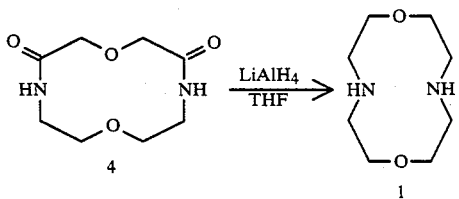

In the above synthesis described by Lehn, diglycolic acid dichloride (2) and 1,5-diamino-3-oxapentane (3) were reacted under high dilution conditions to produce cyclic diamide (4) in 65% yield. The diamide was then reduced with LiAlH₄ to afford diamine 1 in 70% yield.

Cram, et al., "Host-Guest Complexation. 38. Cryptahemispherands and Their Complexes" *J. Am. Chem. Soc., Vol.* 108, No. 11, 1986, pp. 2989–2998, describe synthesis of 1,7-dioxa-4,10-diazacyclododecane at page 2990. 1,5-diamino-3-oxapentane is reacted with 2,2-oxybis(acetyl chloride) at specified concentrations and reaction conditions. Cram, et al. modified the Lehn procedure and increased the yield of the reduction step to 90%.

Dye, et al., "Flow Synthesis. A Substitute for the High-Dilution Steps in Cryptate Synthesis" *J. Org. Chem.*, Vol. 38, No. 9, 1973, pp 1773–1775, describe synthesis of the macrobicyclic polyoxadiamine

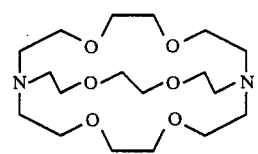

according to Dietrich et al., *Tetrahedron Lett.*, 2885, 2889 (1969). Synthesis of intermediates 6 and 7

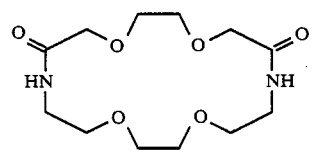

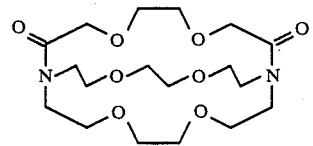

was done using the high-dilution method described by Stetter and Marx, *Justus Liebigs Ann. Chem.*, Vol. 607, p. 59 (1957). Similar procedures are described by Simmons and Park in *J. Amer. Chem. Soc.*, Vol. 90, 2429, 2431, (1986) in synthesis of diazabicycloalkanes and by Lehn and co-workers (*Chem. Commun.*, 1055, (1970); *Tetrahedron Lett.* 4557, (1972); *J. Chem. Soc., Chem. Commun.*, 487 (1972); and *J. Chem. Soc. Chem. Commun.*, 1100 (1972)) in synthesis of macrobicyclic and macrotricyclic ligands.

The procedure used by Dye, et al. requires slow addition with vigorous stirring (over a period of about 8 hours) of dilute (about 0.1M) solutions of the two reagents in benzene into a reaction flask under a nitrogen atmosphere. Dye, et al. found that yields were not greatly reduced by speeding up the addition process, provided that the stirring was sufficiently vigorous.

Fuhrhop and Penzlin, *Organic Synthesis,* Verlag-Chemie (1984) pp. 222–223 give as an example of a high-dilution method a synthesis originally reported by Lehn for preparing a cryptand using highly diluted 1,8-diamino-3,6-dioxactane and 3,6-dioxaoctanedioyl dichloride in benzene. The reaction sequence is shown below:

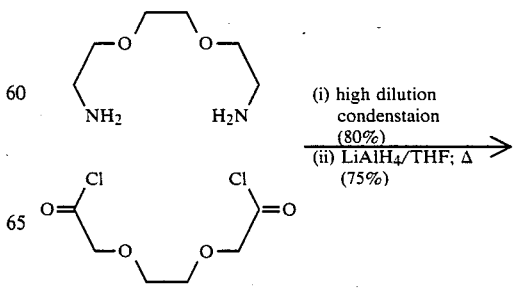

-continued

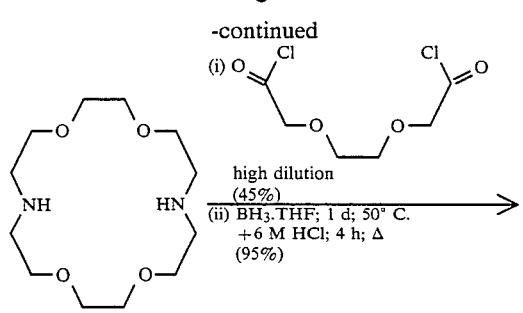

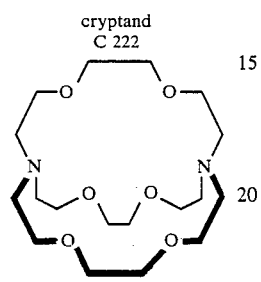

cryptand C 222

The prior art teaches processes for preparing the twelve member diazamonocyclic compound 5,9-dioxo-1,7-dioxa-4,10-diazacyclododecane in small quantities suitable for laboratory experiments; however, such procedure is inappropriate for large scale production of this and similar compounds.

The synthesis of such compounds occurs in a high dilution. The reaction substrates are added at a fixed rate to a comparatively substantially greater volume of solvent, e.g., benzene, over a fixed period of time. The substrates react in the solvent to form the reaction product. In accordance with prior art techniques, to scale up the production of the reaction product, it would be necessary to increase proportionally, the volume of solvent in the reaction to maintain the desired high dilution conditions.

Thus, for example, utilizing the well known Lehn's method for the multigram preparation, one would need about 12 liters of benzene and a suitably sized reactor to produce 66 grams of the cyclic product. By applying the procedure of the present invention, one would only require about 3 liters of the solvent, a smaller reactor and a considerably shorter overall operational time.

Efforts to increase production of the reaction product by increasing concentration of the substrates creates a danger of forming an undesirable linear polymer such as

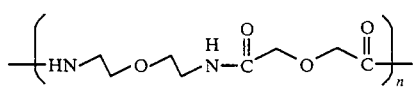

along with the desired reaction product, resulting in lower yield of reaction product and considerable purification effort.

Applicant has discovered that it is possible to continue to add the reaction substrates at predetermined rates to a fixed volume of solvent beyond what would normally be considered possible from the prior art teachings to increase yield of reaction product. The Applicant recognized that the reaction rate of ring closure for a twelve (12) member compound is much faster than that for higher analogs due to fewer degrees of freedom involved in the cyclization step of the smaller twelve (12) member ring. In effect, Applicant is taking advantage of the fact that as the reaction substrates react rapidly to form the reaction product, the concentration of continuously added substrates are held at the low level to maintain the required high dilution conditions.

SUMMARY OF THE INVENTION

The invention is a process for synthesizing large quantities of a compound of formula I

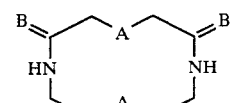

wherein a compound of formula II

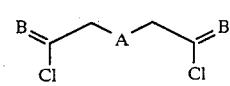

in a solvent e.g. benzene or toluene, is mixed with a compound of formula III

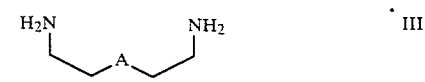

in solvent under suitable process conditions, and wherein A, same or different, is N—R, O, S, CRR' or P(O)R, and R and R' are hydrogen, alkyl, alkylidene, aryl, tosyl, allyl or benzyl, and B is O.

Compounds of formula I may be reduced to form an azacorand of formula IV

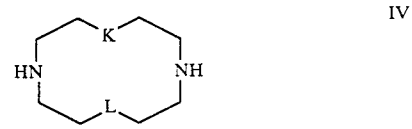

wherein K and L, same or different, are N—R, O, S, CRR', or P(O)R, and R and R' are hydrogen, alkyl, alkylidene, aryl, tosyl, allyl, or benzyl.

Also disclosed is a compound of formula IV synthesized in accordance with the above procedure wherein K and L are not both O or S.

DETAILED DESCRIPTION OF THE INVENTION

The invention is an economical and environmentally desirable process for producing large quantities of compounds of formula I which is an immediate precursor to compounds of formula IV. One possible compound of formula IV, 1,7-dioxa-4,10-diazacyclododecane, an azacorand, is an intermediate used in the synthesis of chromogenic cryptands and cryptahemispherands which have utility in the determination of sodium and potassium biological fluids.

The process of the present invention is a high-dilution reaction between compounds of formulas II and III which rapidly forms compounds of formula I. In accordance with the invention, solutions of each reactant are simultaneously added to a reaction vessel at particular flow rates which vary depending on reactant concentrations and on reaction rate requirements. The reactant of formula II is used in solvent, preferably benzene or toluene, in a concentration range of between about 0.12M and about 0.17M. The reactant of formula III is used in solvent, preferably benzene or toluene, in a concentration range of between about 0.24M and about 0.34M. The solution of reactants of formulas II and III are added simultaneously at a rate of between about 1.5 and about 2.5 ml. per minute to an appropriate volume of solvent to achieve a final dilution of reactants of about 100 times. The reactants in the solvent are violently stirred at about room temperature. The precipitate is then filtered and washed with a solvent, for example, hot chloroform. The filtrates and washings are combined and evaporated to give the compound of formula I.

The compounds of this invention are useful for producing chromogenic cryptahemispherands of the general formula

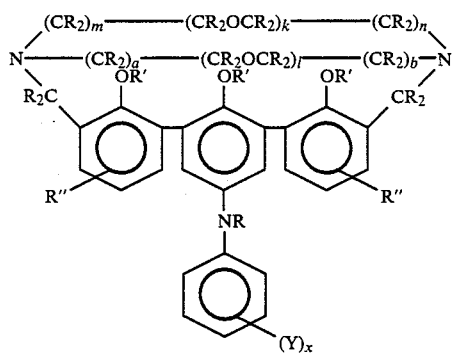

wherein:
R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R", same or different, is hydrogen, lower alkyl, lower alkylidene, lower alkenyl, allyl, aryl or benzyl;
Y is an electron withdrawing group, e.g., CN, $NO_2$, $CF_3$, COOR;
m is 1 to about 3;
n is 1 to about 3;
a is 1 to about 3;
b is 1 to about 3;
k is 1 to about 3;
l is 1 to about 3; and
x is 2 to 4.

The compound of formula V can be formed by coupling an azacorand of formula IV produced according to the present invention

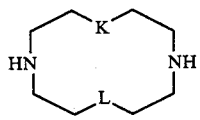

wherein K and L, same or different, are N—R, O, S, CRR', or P(O)R and R and R' are hydrogen, alkyl, alkylidene, aryl, tosyl, allyl, or benzyl, with a compound of formula VI

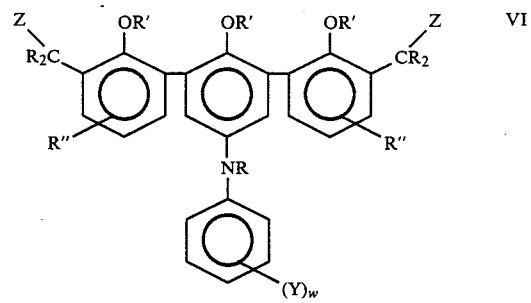

wherein:
R, same or different, is hydrogen, lower alkyl, lower alkylidene, lower alkenyl, allyl, aryl, or benzyl;
R', same or different, is lower alkyl, lower alkylidene, lower alkenyl, allyl, aryl, or benzyl;
R", same or different, is hydrogen, lower alkyl, lower alkylidene, lower alkenyl, aryl or benzyl;
Y is an electron-withdrawing group;
Z is halogen; and
w is 2 to 4.

The compounds of formula IV wherein K and L are not both N—R, O or S can be used in the synthesis of chromogenic cryptahemispherands selective for the transition or heavy metal cations.

The term "lower alkyl", as used in the present disclosure includes an alkyl moiety, substituted or unsubstituted, containing 1-4 carbon atoms. Included in the meaning of lower alkyl are methyl, ethyl, n-propyl, isopropyl, n-butyl and tert-butyl.

"Lower alkylidene" is used herein in the same context as "lower alkyl", but designates an alkylene group (i.e., a divalent alkyl) having 1-4 carbon atoms. The term lower alkylidene includes, but is not limited to, methylene, ethylidene, n-propylidene, iso-propylidene, n-butylidene, sec-butylidene and tert-butylidene.

The term "aryl" as used herein includes substituted or unsubstituted aryl moieties containing 6-12 carbon atoms, such as, for example, phenyl, tolyl, butyl phenyl, naphthyl ethyl, chlorophenyl, nitrophenyl and carboxyphenyl.

"Lower alkenyl" as used herein designates a lower alkenyl moiety, substituted or unsubstituted, having 1-4 carbon atoms and includes, for example, ethenyl, 1-propenyl, 2-propenyl, isopropenyl, 1-butenyl, 2-butenyl, 3-butenyl, isobutenyl and tert-butenyl.

The term "alkyl" as used in the present disclosure includes substituted or unsubstituted moieties containing from 1 to 12 carbon atoms, and includes for example, methyl, butyl, isobutyl and octyl.

The term "allyl" as used in the present disclosure includes substituted or unsubstituted moieties containing from 3 to 12 carbon atoms, such as, for example, 2-propene, 2-methylpropene and 2-butene.

The term "alkylidene" designates substituted or unsubstituted moieties containing from 2 to 12 carbon atoms, and includes for example, 1,2-ethylidene, 1,2-propylidene, 3,4-hexylidene.

The above moieties may be unsubstituted or substituted as noted providing any such substituents do not interfere with the operation or functioning of the presently claimed invention.

The following working examples describe experiments which were performed in developing the present invention. Standard commercially available reagent grade chemicals were used whenever possible. These working examples are to be considered illustrative of the present invention and should not be interpreted as limiting its scope.

EXAMPLE 1

Following the reaction scheme

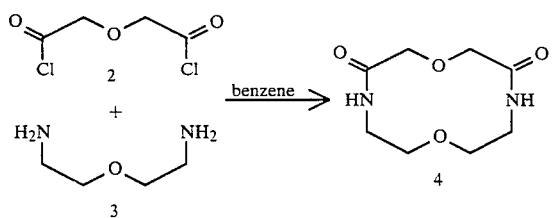

a solution (500 ml) of 2,2-oxybis(acetyl chloride) (2) (24.5 g, 0.14 mole) in anhydrous benzene and a solution (500 ml) of 1,5-diamino-3-oxapentane (3) (30.0 g, 0.28 mole) in anhydrous benzene were added simultaneously to 1 liter of violently stirred anhydrous benzene at a rate of 2.5 ml per minute at room temperature. The precipitate was filtered and washed with hot CHCl$_3$, and the filtrates were evaporated to give a residue which was recrystallized from chloroform-heptane to afford 15.5 g (58%) of 5,9-dioxo-1,7-dioxa-4,10-diazacyclododecane, mp 169°–171° C.

EXAMPLE 2

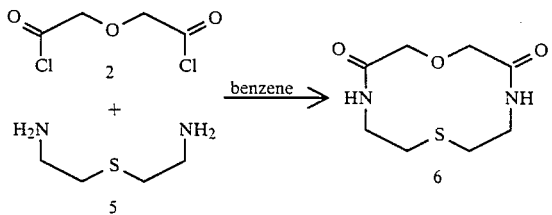

A solution (100 ml) of 2,2-oxybis(acetyl chloride) (2) (5.53 g, 32.3 mmol) in benzene and a solution (100 ml) of 1,5-diamino-3-thiapentane (5) (7.70 g, 64.0 mmol) in benzene were simultaneously added to 250 ml of violently stirred anhydrous benzene at a rate of 1.64 ml per minute at room temperature. The precipitate was collected and washed with hot CHCl$_3$. The filtrate and washings were combined and the solvent was evaporated to give 3.86 g (55%) of 5,9-dioxo-1-oxa-7-thia-4,10-diazacyclododecane (6) as a white solid, mp. 186°–188° C. Analysis calculated for C$_8$H$_{14}$N$_2$SO$_3$: C, 44.02; H, 6.46. Found: C, 43.97; H, 6.44%.

EXAMPLE 3

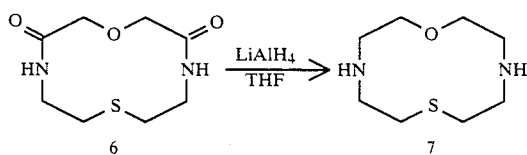

To a suspension of lithium aluminum hydride (3.12 g, 82.2 mmol) in refluxing tetrahydrofuran under argon was added diamide 6 (3.50 g, 16.0 mmol) in small portions over 1 hour period. The mixture was refluxed for 3 days. After cooling to room temperature the excess reagent was destroyed by adding a mixture of water (2.7 ml) and THF (6.2 ml), then 15% aqueous NaOH (3.4 ml) and another mixture of water (5.6 ml) and THF (3.4 ml). The solid was filtered and washed extensively with pure THF. The filtrate and washings were combined, the solvent was removed in vacuo and the residue was chromatographed through a short alumina column with chloroform and the product was recrystallized from a chloroform-hexane mixture to give 1.88 g (62%) of 1-oxa-7-thia-4,10-diazacyclododecane (7) as a white solid mp 74°–76° C. Analysis calculated for C$_8$H$_{18}$N$_2$OS: C, 50.49; H, 9.53. Found: C, 50.18; H, 9.72%.

It should be understood by those skilled in the art that various modifications may be made in the present invention without departing from the spirit and scope thereof as described in the specification and defined in the amended claims.

What is claimed is:

1. A process for preparing a compound of formula I

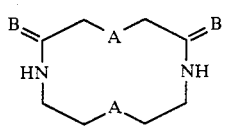

wherein a solvent solution of a compound of formula II

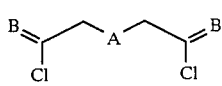

is mixed with a solvent solution of a compound of formula III

under suitable process conditions, wherein A, same or different, is N—R, O, S, CRR' or P(O)R, and R and R' are hydrogen, alkyl, alkylidene, aryl, tosyl, allyl or benzyl, and B is O.

2. The process of claim 1 wherein A is O and B is O.

3. The process of claim 1 wherein the compound of formula II—solvent solution and the compound of formula III—solvent solution are simultaneously added to a reaction vessel containing solvent.

4. The process of claim 3 wherein the reaction vessel solvent is benzene or toluene.

5. The process of claim 3 wherein the compound of formula II is concentrated in benzene in a range of between about 0.12M and about 0.17M.

6. The process of claim 5 wherein the solvent is benzene or toluene.

7. The process of claim 3 wherein the compound of formula III is concentrated in solvent in a range of between about 0.24M and about 0.34M.

8. The process of claim 7 wherein the solvent is benzene or toluene.

9. The process of claim 3 wherein addition of the compound of formula II—solvent solution is at a rate of between about 1.5 and about 2.5 ml per minute.

10. The process of claim 3 wherein addition of the compound of formula III—solvent solution is at a rate of between about 1.5 and about 2.5 ml per minute.

11. A process for preparing an azacorand of formula IV

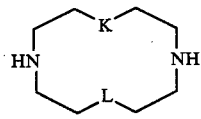

wherein K and L, same or different, are N—R, O, S, CRR', or P(O)R, and R and R' are hydrogen, alkyl, alkylidene, allyl, aryl, benzyl or tosyl, comprising:
  (a) forming the compound of formula I according to the process of claim 1; and
  (b) reducing the compound of step (a).

12. A compound of formula IV wherein K and L are not both O or S.

13. A process for preparing a chromogenic cryptahemispherand of formula V

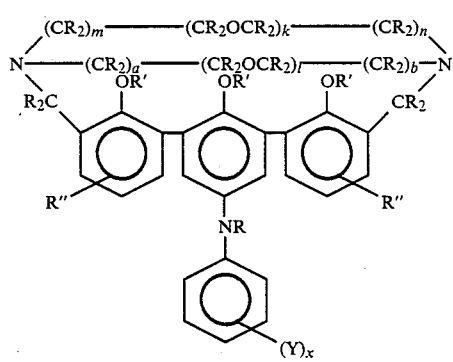

wherein:

R, same or different, is hydrogen, lower alkyl, lower alkylidene, lower alkenyl, allyl, aryl or benzyl;
R', same or different, is lower alkyl, lower alkylidene, lower alkenyl, allyl, aryl or benzyl;
R", same or different, is hydrogen, lower alkyl, lower alkylidene, lower alkenyl, allyl, aryl or benzyl;
Y is an electron withdrawing group, e.g., CN NO$_2$, CF$_3$, COOR;
m is 1 to 3;
n is 1 to 3;
a is 1 to 3;
b is 1 to 3;
k is 1 to 3;
l is 1 to 3; and
x is 2 to 4;

wherein an azacorand formed as in claim 11 is coupled with the following compound VI

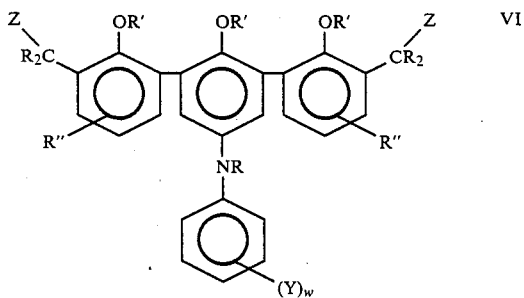

wherein:
R, same or different, is hydrogen, lower alkyl, lower alkylidene, lower alkenyl, allyl, aryl or benzyl;
R", same or different, is lower alkyl, lower alkylidene, lower alkenyl, allyl, aryl or benzyl;
R", same or different, is hydrogen, lower alkyl, lower alkylidene, lower alkenyl, aryl or benzyl;
Y is an electron withdrawing group;
Z is halogen; and
w is 2 to 4.

* * * * *